United States Patent [19]

Bartsch et al.

[11] Patent Number: 5,221,737

[45] Date of Patent: Jun. 22, 1993

[54] GENE AND GENE STRUCTURE CODING FOR AN AMINOTRANSFERASE, AND MICROORGANISMS WHICH EXPRESS THIS GENE

[75] Inventors: Klaus Bartsch, Steinbach; Arno Schulz, Hattersheim am Main; Eugen Uhlmann, Glashütten/Taunus, all of Fed. Rep. of Germany

[73] Assignee: Hoechst Aktiengesellschaft, Frankfurt am Main, Fed. Rep. of Germany

[21] Appl. No.: 450,230

[22] Filed: Dec. 13, 1989

[30] Foreign Application Priority Data

Dec. 15, 1988 [DE] Fed. Rep. of Germany ....... 3842174
Sep. 26, 1989 [DE] Fed. Rep. of Germany ....... 3932015

[51] Int. Cl.⁵ ............................................ C07H 15/12
[52] U.S. Cl. .................................. 536/23.2; 435/71.2; 435/320.1; 435/849; 935/24; 935/29; 935/73; 935/56

[58] Field of Search ..................... 536/27, 71.1, 71.2, 536/172.3, 320.1, 849; 935/24, 29, 55, 56, 73

[56] References Cited

U.S. PATENT DOCUMENTS

4,968,609  11/1990  Ito et al. ........................... 435/69.1
5,017,481   5/1991  Matsui et al. ....................... 435/108

Primary Examiner—Amelia Burgess Yarbrough
Attorney, Agent, or Firm—Finnegan, Henderson, Farabow, Garrett & Dunner

[57] ABSTRACT

A gene and gene structure coding for an aminotransferase, and microorganisms which express this gene The preparation of L-2-amino-4-methylphosphinobutyric acid (L-PPT) by transamination of (3-carboxy-3-oxopropyl)-methylphosphinic acid with the aid of the L-PPT-specific transaminase from *E. coli* DH 1 is very much more efficient when the gene coding for this enzyme is isolated, incorporated into a plasmid and then a microorganism is transformed therewith.

8 Claims, 10 Drawing Sheets

```
ATG AAC AGC AAT AAA GAG TTA ATG CAG CGC AGT CAG GCG ATT
Met Asn Ser Asn Lys Glu Leu Met Gln Arg Ser Gln Ala Ile
                289                 304                 319

CCC CGT GGC GTT GGG CAA ATT CAC CCG ATT TTC GCT GAC CGC GCG
Pro Arg Gly Val Gly Gln Ile His Pro Ile Phe Ala Asp Arg Ala
                334                 349                 364

GAA AAC TGC CGG GTG TGG GAC GTT GAA GGC CGT GAG TAT CTT GAT
Glu Asn Cys Arg Val Trp Asp Val Glu Gly Arg Glu Tyr Leu Asp
                379                 394                 409

TTC GCG GGG ATT GCG GGC GTG CTC AAT ACC GGG CAC CTG CAT CCG
Phe Ala Gly Ile Ala Gly Val Leu Asn Thr Gly His Leu His Pro
                424                 439                 454

AAG GTG GTG GCC GTG GAA GCG CAG TTG AAA AAA CTG TCG CAC
Lys Val Val Ala Val Glu Ala Gln Leu Lys Lys Leu Ser His
                469                 484                 499

ACC TGC TTC CAG CTG GCT TAC GAG CCG TAT CTG GAG CTG TGC
Thr Cys Phe Gln Val Leu Ala Tyr Glu Pro Tyr Leu Glu Leu Cys
                514                 529                 544

GAG ATT ATG AAT CAG AAG GTG CCG GGC GAT TTC GCC AAG AAA ACG
Glu Ile Met Asn Gln Lys Val Pro Gly Asp Phe Ala Lys Lys Thr
                559                 574                 589

FIG. 6a
```

```
                         604                         619                         634
CTG CTG GTT ACG ACC GGT TCC GAA GCG GTG GAA AAC GCG GTA AAA
Leu Leu Val Thr Thr Gly Ser Glu Ala Val Glu Asn Ala Val Lys 649                         664                         679
ATC GCC CGC GCC ACC AAA CGT AGC GGC ACC ATC GCT TTT AGC
Ile Ala Arg Ala Thr Lys Arg Ser Gly Thr Ile Ala Phe Ser 694                         709                         724
GGC GCG TAT CAC CGG CGC ACG CAT TAC CTG GCG CTG ACC GGC
Gly Ala Tyr His Gly Arg Thr His Tyr Leu Ala Leu Thr Gly 739                         754                         769
AAG GTG AAT CCG TAC TCT GCG GGG CTG ATG CCG GGT CAT
Lys Val Asn Pro Tyr Ser Ala Gly Met Leu Met Pro Gly His 784                         799                         814
GTT TAT CGC GCG CTT TAT CCT TGC CCG CTG CAC GGC ATA AGC GAG
Val Tyr Arg Ala Leu Tyr Pro Cys Pro Leu His Gly Ile Ser Glu 829                         844                         859
GAT GAC GCT ATC GCC AGC ATC CAC CGG ATC TTC AAA AAT GAT GCC
Asp Asp Ala Ile Ala Ser Ile His Arg Ile Phe Lys Asn Asp Ala 874                         889                         904
GCG CCG GAA GAT ATC GCC GCC ATC GTG ATT GAG CCG GTT CAG GGC
Ala Pro Glu Asp Ile Ala Ala Ile Val Ile Glu Pro Val Gln Gly
```

FIG. 6b

```
          919                934                949
GAA GGC GGT TTC TAC GCC TCG TCG CCA GCC TTT ATG CAG CGT TTA
Glu Gly Gly Phe Tyr Ala Ser Ser Pro Ala Phe Met Gln Arg Leu 964                979                994
CGC GCT CTG TGT GAC GAG CAC GGG ATC ATG CTG ATT GCC GAT GAA
Arg Ala Leu Cys Asp Glu His Gly Ile Met Leu Ile Ala Asp Glu 1009               1024               1039
GTG CAG AGC GGC GCG GGG CGT ACC GGC ACG CTG TTT GCG ATG GAG
Val Gln Ser Gly Ala Gly Arg Thr Gly Thr Leu Phe Ala Met Glu 1054               1069               1084
CAG ATG GGC GTT GCG CCG GAT CTT ACC ACC TTT GCG AAA TCG ATC
Gln Met Gly Val Ala Pro Asp Leu Thr Thr Phe Ala Lys Ser Ile 1099               1114               1129
GCG GGC GGC TTC CCG CTG GCG GGT CTG ACC GGG CGC GCG GAA GTA
Ala Gly Gly Phe Pro Leu Ala Gly Val Thr Gly Arg Ala Glu Val 1144               1159               1174
ATG GAT GCC GTC GCT CCA GGC GGC CTG GGC ACC TAT GCG GGT
Met Asp Ala Val Ala Pro Gly Gly Leu Gly Gly Thr Tyr Ala Gly 1189               1204               1219
AAC CCG ATT GCC TGC GTG GCT GCG CTG GAA GTG TTG AAG GTG TTT
Asn Pro Ile Ala Cys Val Ala Ala Leu Glu Val Leu Lys Val Phe
```

FIG. 6c

```
                                                                    1264
GAG CAG GAA AAT CTG CAA AAA GCC AAC GAT CTG GGG CAG AAG
Glu Gln Glu Asn Leu Gln Lys Ala Asn Asp Leu Gly Gln Lys 1279                                                           1309
TTG AAA GAC GGA TTG CTG GCG ATA GCC GAA AAA CAC CCG GAG ATC
Leu Lys Asp Gly Leu Leu Ala Ile Ala Glu Lys His Pro Glu Ile 1324                                                           1354
GGC GAC GTA CGC GGG CTG GGG GCG ATG ATC GCC ATT GAG CTG TTT
Gly Asp Val Arg Gly Leu Gly Ala Met Ile Ala Ile Glu Leu Phe 1369                                                           1399
GAA GAC GAT CAC AAC AAG CCG GAC GCC AAA CTC ACC GCC GAG
Glu Asp Gly Asp His Asn Lys Pro Asp Ala Lys Leu Thr Ala Glu 1414                                                           1444
ATC GTG GCT CGC GCC CGC GAT AAA GGC CTG ATT CTT CTC TCC TGC
Ile Val Ala Arg Ala Arg Asp Lys Gly Leu Ile Leu Leu Ser Cys 1459                                                           1489
GGC CCG TAT TAC AAC GTG CTG CGC ATC CTT GTA CCG CTC ACC ATT
Gly Pro Tyr Tyr Asn Val Leu Arg Ile Leu Val Pro Leu Thr Ile 1504                                                           1534
GAA GAC GCT CAG CGT CAG GGT CTG GAG ATC ATC AGC CAG TGT
Glu Asp Ala Gln Arg Gln Gly Leu Glu Ile Ile Ser Gln Cys
```

FIG. 6d

```
                              1549
TTT GAT GAG GCG AAG CAG TAG
Phe Asp Glu Ala Lys Gln ***
```

FIG. 6e

GENE AND GENE STRUCTURE CODING FOR AN AMINOTRANSFERASE, AND MICROORGANISMS WHICH EXPRESS THIS GENE

CROSS-REFERENCE TO RELATED APPLICATION

U.S. patent application Ser. No. 07/359,591, filed Jun. 1, 1989, corresponds to (and claims priority of) German Patent Application P 38 18 851.1 (to be published on or about Dec. 7, 1989, as German Offenlegungsschrift DE 3,818,851 A1) and European Patent Application EP-A2 0,344,683, to be published on Dec. 6, 1989.

German Offenlegungsschrift 38 18 851 (which has not been prior-published and corresponds to EP-A2 0 344 683 published on Dec. 6, 1989) has already proposed an aminotransferase (transaminase) which was isolated from E. coli DH-1.

The gene which codes for this new transaminase has now been found. It is possible thereby, according to the invention, to prepare the enzyme in larger amounts than in accordance with the earlier proposal, but also to carry out the specific transamination reactions with a microorganism transformed according to the invention. Thus, the isolation and characterization of the gene permits very much more efficient transaminations than are possible with the enzyme isolated according to the earlier proposal.

German Offenlegungsschrift 38 18 581 characterizes the new enzyme, inter alia, by the amino acid sequence of the N terminus. The first 30 of these amino acids are shown below:

```
          1            5            10              15
NH2 —MET ASN SER ASN LYS GLU LEU MET GLN ARG ARG SER GLN ALA ILE 16           20           25              30
    PRO ARG GLY VAL GLY GLN ILE HIS PRO ILE PHE ALA ASP ARG ALA
```

In the region of amino acids 4 to 10 there are methionine, which is coded for by only one triplet, as well as four amino acids which are encoded by only two triplets. Only leucine is six-fold "degenerate" in the genetic code. This sequence is thus particularly well suited for the construction of a probe of 20 nucleotides (20mer):

```
5—AAC AAA GAA TTA ATG CAA CG—3
       T   G  GC G       GA
               C
               T
```

This probe was synthesized by the phosphoramidite method in a manner known per se. Additionally synthesized was a 38mer of the non-coding strand for amino acids 15 to 27.

```
3-TAG GGC GCG CCG CAA CCG GTC TAG GTG GGC TAG AAG CG-5
       T       T       T           T
```

This oligonucleotide was also synthesized by the phosphoramidite method.

Figure 1:
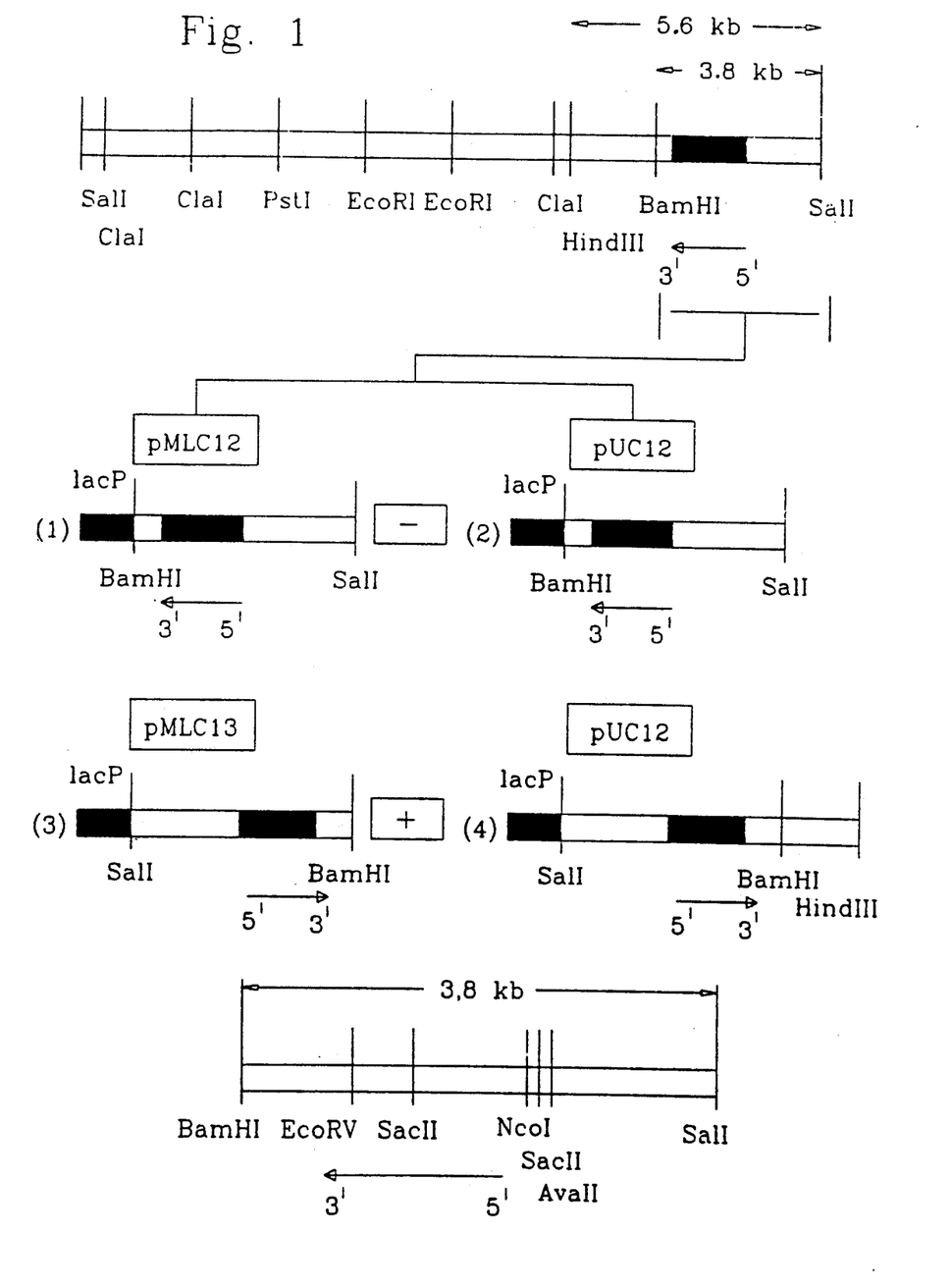
FIG. 1 shows the localization of the gene according to the invention onto a DNA fragment 3.8 kb in size.

These probes were employed to screen a cosmid gene bank of E. coli DH 1. Hybridization-positive clones were initially assayed for elevated L-PPT transaminase activity and then characterized in detail by restriction mapping. It was possible by subcloning and activity assays of subfragments to localize the position of the gene in the genome and subsequently to define it even further by exonuclease degradation. Thus, initially a 15 kb SalI fragment on which the gene according to the invention is located was identified, as was a 3.8 kb SalI/-BamHI fragment which allowed the orientation of the gene to be established (FIG. 1). The latter fragment also contains the gene's own promoter. It was thus possible, merely by cloning restriction fragments into suitable vectors, to increase the transaminase activity by about fifty times compared with the starting strain.

The yield of enzyme or enzyme activity can also be influenced by choosing suitable culture conditions. Thus, for example, the glucose content in the medium plays a considerable role, depending on the choice of the expression system: at concentrations above 0.05% there may be a drastic fall in the enzyme activity. This dependence is evident even with control strains which express only the copy of the transaminase gene in the bacterial chromosome.

In a further development of this concept of the invention, it was then possible to localize the gene coding for the aminotransferase more accurately: the gene is located on a 1.6 kb DraI/BamHI fragment (FIG. 2) which contains an open reading frame which is 1281 nucleotides long (including the stop codon) and codes for a protein of 426 amino acids.

The DNA sequence is depicted in Table 1. The ATG start codon starts with nucleotide no. 275, and the TAG stop codon starts with nucleotide no. 1553.

FIG. 6 shows the coding strand of the gene as well as the amino acid sequence of the transaminase according to the invention. The latter shows only a few homologies of sequence with the other known transaminases from E. coli (aspC, tyrB, hisC, ilvE, avtA and serC).

Because of the substrate specificity of the L-PPT transaminase for 4-aminobutyric acid (GABA) and comparison of the restriction map of the 15 kb SalI fragment (see FIG. 1) with the physical map of the E. coli K-12 genome [Kohara et al. (1987), Cell 50: 495–508], it was possible to identify the cloned transaminase gene as gabT, a locus from the E. coli K-12 gab cluster at 57.5 min [Metzer et al. (1979), J. Bacteriol. 137; 1111–1118].

Knowledge of the gene allows the structural gene to be provided with strong promoters in a directed manner. The gene constructs obtained in this way not only show higher expression rates than the previously mentioned expression plasmids but also permit their activity to be controlled by inducers. It is furthermore possible to choose expression systems which exhibit no catabolite repression, such as the tac system so that bacteria transformed with such gene constructs can also be fermented in the presence of glucose in the nutrient medium. This makes high cell densities possible and thus achieves high yields relative to the fermenter volume.

Hence the invention relates to a gene for a transaminase specific for L-2-amino-4-methylphosphinobutyric acid (L-PPT), located on a 1.6 kb DraI/BamHI fragment from the genome of E. coli DH 1, having the DNA sequence shown in FIG. 6 and, furthermore, to a gene coding for an enzyme having the amino acid sequence shown in FIG. 6 as well as for enzymes which have the same action and whose amino acid sequence is derived from that shown in FIG. 6 by addition, deletion or exchange of amino acids.

The invention additionally relates to a transaminase specific for L-2-amino-4-methylphosphinobutyric acid (L-PPT) and has an amino acid sequence which is derived from that shown in Table 2 by addition, deletion or exchange of amino acids.

The invention furthermore relates to plasmids containing a gene of this type, and to microorganisms, in particular E. coli, containing a plasmid of this type.

The invention also relates to a process for the stereoselective production of L-PPT from (3-carboxy-3-oxopropyl)-methylphosphinic acid by transamination with microorganisms, which comprises employing a microorganism which is transformed with one of the plasmids specified above, or wherein an enzyme which is modified (as above) by modification of the amino acid sequence is employed.

The invention is explained in detail in the examples which follow. Percentage data in these relate to weight.

EXAMPLE 1

Cloning of the L-PPT transaminase gene from E. coli DH 1/ construction of expression plasmids Chromosomal DNA from E. coli DH 1 was isolated by the method described in Ausubel et al. (1987), Current Protocols in Molecular Biology: 5.3.2.–5.4.3., 5.7.1.–5.7.3., partially cleaved with Sau3A and fractionated by size in an agarose gel. DNA fragments about 25–40 kb in size were ligated into the cosmid vector pTBE [Grosveld, F. G. et al. (1982), Nucleic Acids Research 10: 6715] which had been cut with BamHI and were packaged into lambda phages Amersham: in vitro packaging system for Lambda DNA, Code No. 334Z, and Maniatis et al. (1982), Molecular Cloning, A Laboratory Manual, Cold Spring Harbor: 296–299]. Transfection of the recipient strain E. coli DH 1 was followed by isolation of 2000 single clones, which corresponds to several genome-equivalents of E. coli. Two oligonucleotides corresponding to regions of the N-terminal amino acid sequence of the L-PPT transaminase protein (20mer and 38mer, see text) were synthesized in order to find the gene which was sought in the cosmid gene bank which had been constructed.

Subsequently the cosmids isolated from the single clones were bound (in accordance with Maniatis et al.: 331) to nitrocellulose filters (Schleicher and Schüll BA85) with the aid of a PRL Dot-Plot suction apparatus and were hybridized with the 32P-end-labeled oligonucleotides (Ausubel et al.: 6.4.1.–6.4.4.). 2 of 4 hybridization-positive clones showed a 3- to 5-fold increase in activity in the L-PPT transaminase enzyme assay (see below, Example 2). The two clones contained an identical 15 kb SalI insertion whose restriction map is depicted in FIG. 1.

A 5.6 kb HindIII/SalI fragment and a 3.8 kb BamHI/SalI fragment from this DNA segment, both of which hybridized with the 5'-specific oligonucleotides of L-PPT transaminase, were cloned in both orientations behind the E. coli lac promoter into the vectors pUC12 and pMLC12/13 [Perbal, B. (1984), A Practical Guide to Molecular Cloning: 259–272], and the recombinant plasmids were subsequently assayed for transaminase activity (FIG. 1). Whereas the enzyme activities of the constructs (1) and (2) were only a little above the background, the L-PPT transaminase expression shown by (3) and (4) (pTrans2 and pTrans3, FIG. 3), which contained the same DNA fragment in the opposite orientation to the lac promoter, conferred to (1) and (2), was increased about 50-fold. It was possible to establish from this the direction of transcription of the gene, as depicted in FIG. 1.

The location of the transaminase gene on the 3.8 kb BamHI/SalI fragment was established more accurately by further restriction mapping as well as by preparing a series of ExoIII/S1 deletions [Henikoff, S. (1984), Gene 28: 351–359]. In the latter method the 3.8 kb fragment cloned into pMLC12/13 was subjected to enzymatic digestion, in each case starting from one end, for various lengths of time. The truncated insertions were subsequently assayed for enzymatic activity. On the assumption that parts of the transaminase structural gene had been deleted in DNA fragments which no longer had activity, it was possible to establish the location of the gene, as shown in FIG. 1 below.

Figure 3A:
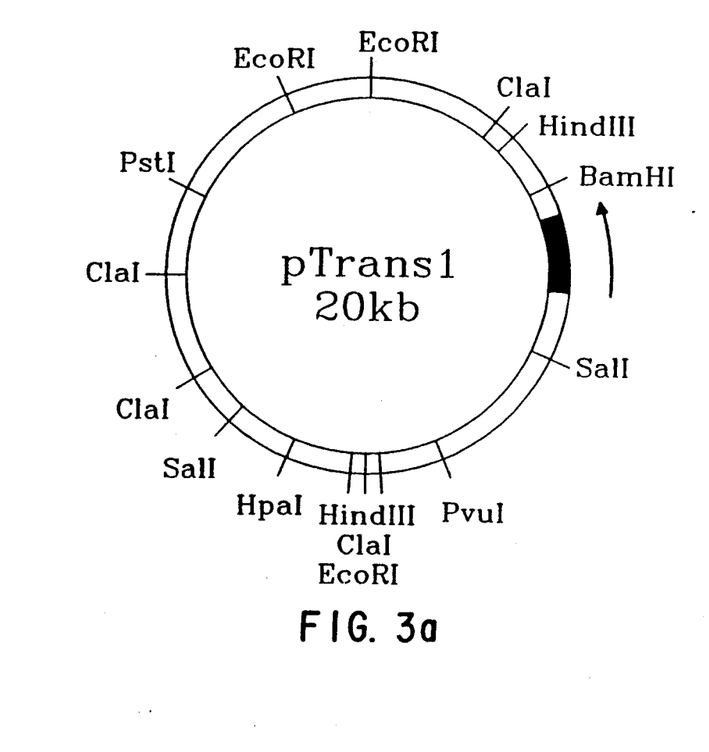
FIGS. 3a, b, and c show shows the initially developed vectors pTrans1, pTrans2 and pTrans3.
Figure 3B:
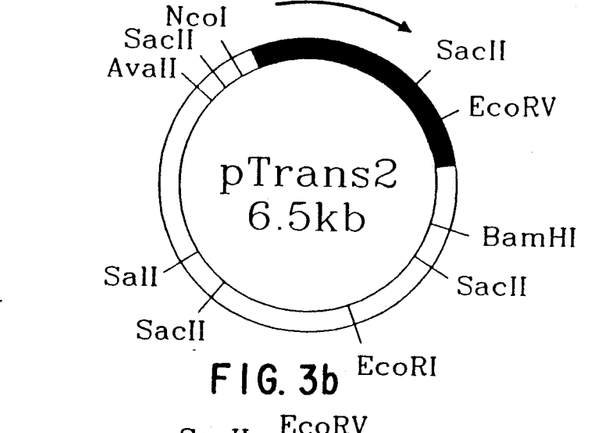
Figure 3C:
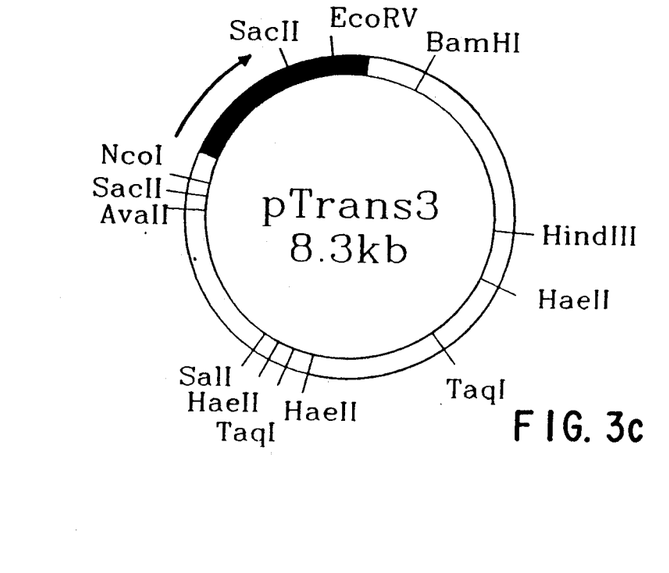

FIG. 3 depicts three different recombinant plasmids which carry the cloned L-PPT transaminase gene from E. coli DH 1 and are used in the Examples which follow. The plasmid pTrans1 contains the 15 kb SalI insert in the cosmid vector pTBE and expresses the transaminase under the control of the endogenous promoter. The two other constructs are expression plasmids with the E. coli lac promoter: pTrans2 contains the 3.8 kb BamHI/SalI fragment in pMLC13, pTrans3 contains the 5.6 kb HindIII/SalI fragment in pUC12.

EXAMPLE 2

L-PPT production in E. coli DH 1 with various transaminase expression plasmids

E. coli DH 1 transformants with the recombinant plasmids pTrans1, pTrans2 and pTrans3 and with the vector plasmids pTBE, pMLC13 and pUC12 as control were cultured in 10 ml cultures in LB medium [Luria-Bertani Medium, Maniatis et al. (1982): 68] with 50 μg of the appropriate antibiotic (ampicillin in the case of pTrans1, pTrans3, pTBE and pUC12, and chloramphenicol in the case of pTrans2 and pMLC13) at 37° C. for 15 h. The cells were then removed by centrifugation at 5000×g for 5 min, washed twice in 5 ml each time of 10 mM NaCl, 10 mM sodium phosphate (pH=7.5) and resuspended for the transaminase activity assay in 1 ml of reaction mix (5 mM NaCl, 5 mM sodium phosphate, 30 g/l (3-carboxy-3-oxopropyl)-methylphosphinic acid, 90 g/l L-glutaminic acid, 100 mM Tris/HCl, pH=8.0). The cells were incubated in this solution while shaking at 37° C. for 1 h and then denatured at 95° C. for 10 min. The reaction supernatants were analyzed for L-PPT production in an amino acid analyzer (Biotronic Amino Acid Analyzer LC 5001, 3.2×130 mm BTC-2710 column).

The space-time yields achieved with the various constructs are compiled in Tab. 2. By far the highest enzyme activites were achieved with the two lac expression plasmids, with the result for the pUC12 derivative pTrans3 being even better, presumably because of the larger copy number per cell, than for the pMLC13 derivative pTrans2. The space-time yields measured for pTrans3 were about 60 times higher than the results for the control cells transformed with pUC12 vector plasmid.

TABLE 2

L-PPT production in E. coli DH 1 with various transaminase expression plasmids

| Plasmid: | Space-time yield (mg of L-PPT produced/1/h): |
|---|---|
| pTBE | 100 |
| pMLC13 | 60 |
| pUC12 | 70 |
| pTrans1 | 300 |
| pTrans2 | 2400 |
| pTrans3 | 4300 |

EXAMPLE 3

Effect of the glucose concentration in the culture medium on the L-PPT transaminase activity E. coli DH 1-pTrans3 and E. coli DH 1-pUC12 were cultured in 10 ml of LB medium without glucose and with increasing glucose concentrations (0.01%, 0.05%, 0.1% and 0.5%), worked up and assayed for L-PPT transaminase activity as in Example 2. The result is shown in Tab. 4. Both the lac-expressed transaminase gene on the plasmid pTrans3 and the chromosomal gene from the control strain (with pUC12) were repressed by glucose concentrations >0.05% The maximum rate of L-PPT synthesis was achieved with 0.05% glucose in the medium.

TABLE 3

Dependence of the L-PPT transaminase activity in E. coli DH-1 on the glucose concentration in the culture medium

| Glucose concentration in the medium (%) | Rel. transaminase activity (%) | |
|---|---|---|
| | pUC12 | pTrans3 |
| 0 | 8 | 100ª |
| 0.01 | 18 | 184 |
| 0.05 | 22 | 276 |
| 0.1 | 12 | 18 |
| 0.5 | 2 | 8 |

ªThe activity of pTrans3 without glucose was set equal to 100%.

EXAMPLE 4

Overexpression of L-PPT transaminase protein from E. coli DH 1

E. coli DH 1-Trans3 and E. coli DH 1-pUC12 were cultured as in Example 3. The cells were washed and resuspended in 1 ml of 10 mM NaCl, 10 mM sodium phosphate (pH=7.5) and then disrupted by sonication for 5×20 sec., and aliquots of these crude extracts, with equal amounts of protein, were applied to a 12.5% SDS/polyacrylamide gel [Laemmli, U.K. (1970), Nature 227: 680].

The overexpressed L-PPT transaminase protein appears in the protein pattern of extracts from E. coli DH 1-pTrans3 as an additional band of 43,000 Dalton. This is absent in the expression strain in the sample with 0.5% glucose in the culture medium as well as in the control strain E. coli DH 1-pUC12 with 0.05% glucose.

EXAMPLE 5

Sequencing of the L-PPT transaminase gene from E. coli K12

Figure 2:
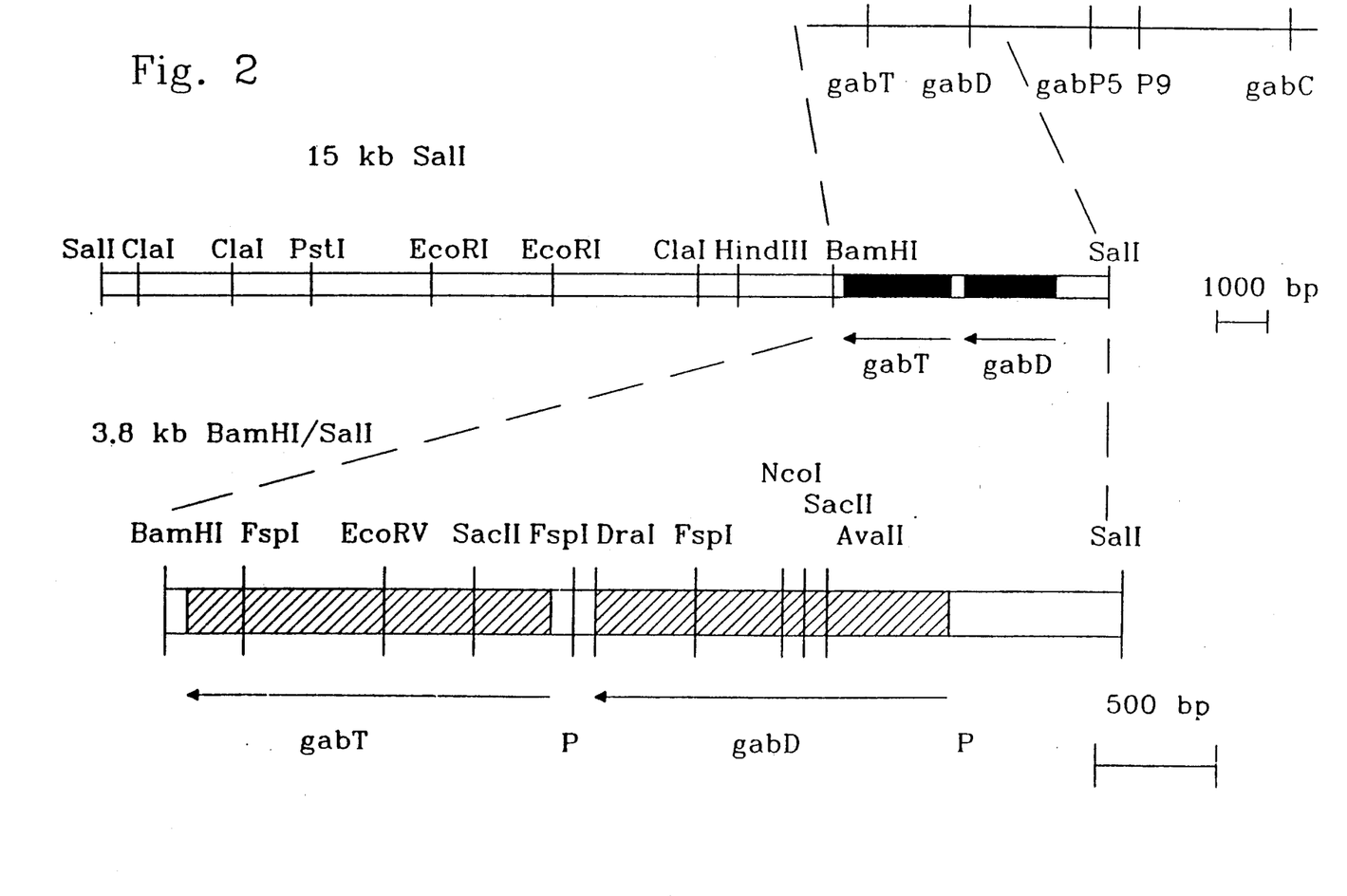
FIG. 2 demonstrates that this fragment contains another gene (gab D) besides the desired gene (gab T).

It was possible, further subcloning and activity assays of restriction fragments of the 3.8 kb BamHI/SalI fragment, to localize the L-PPT transaminase gene to a 1.6 kb DraI/BamHI DNA fragment (FIG. 2). The latter was sequenced by the dideoxy method [Sanger, F. et al. (1977), Proc. Natl. Acad. Sci. USA 74: 5463-5468]with α-[35S]-dATP and double-stranded DNA as templates [Chen, E. Y. and Seeburg: P. H. (1985): DNA 4: 165-170]. For this purpose, deletions prepared by ExoIII/S1 nuclease digestion and starting from the 3' end (BamHI cleavage site) of the gene [Henikoff, S. (1984), Gene 28: 351-359], as well as a number of restriction fragments of the 1.6 kb DraI/BamHI fragment, were cloned in a known manner [Maniatis et al. (1982), Molecular Cloning, A Laboratory Manual, Cold Spring Harbor] into the vectors pMLC12/13 and pUC12/13 and sequenced with commercially available primers (from the pUC sequencing kit, Boehringer Mannheim, Order No. 1013 106). In addition, synthetic oligonucleotides which it was possible to prepare (phosphoramidite method) on the basis of sequence information already available were also used as sequencing primers. The exact restriction map of the 1.6 kb DraI/BamHI fragment is shown in FIG. 2.

EXAMPLE 6

Preparation of expression plasmids with the L-PPT transaminase structural gene from E. coli K-12 a) lac expression plasmids

Figure 4A:
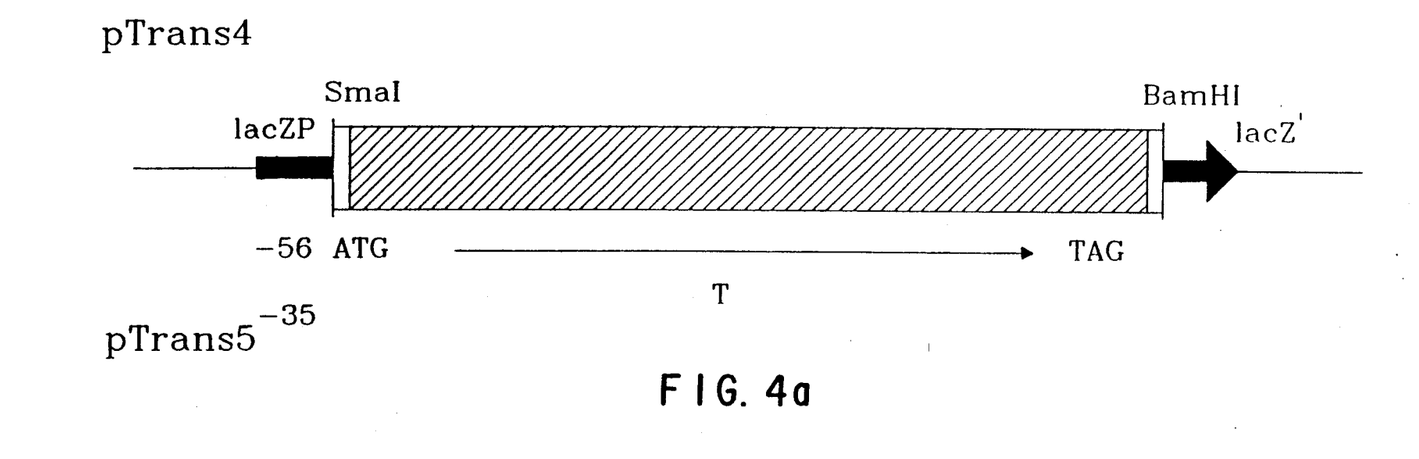
FIGS. 4a and b show shows the location of the gene according to the invention in the vectors pTrans4 to pTrans7.
Figure 4B:
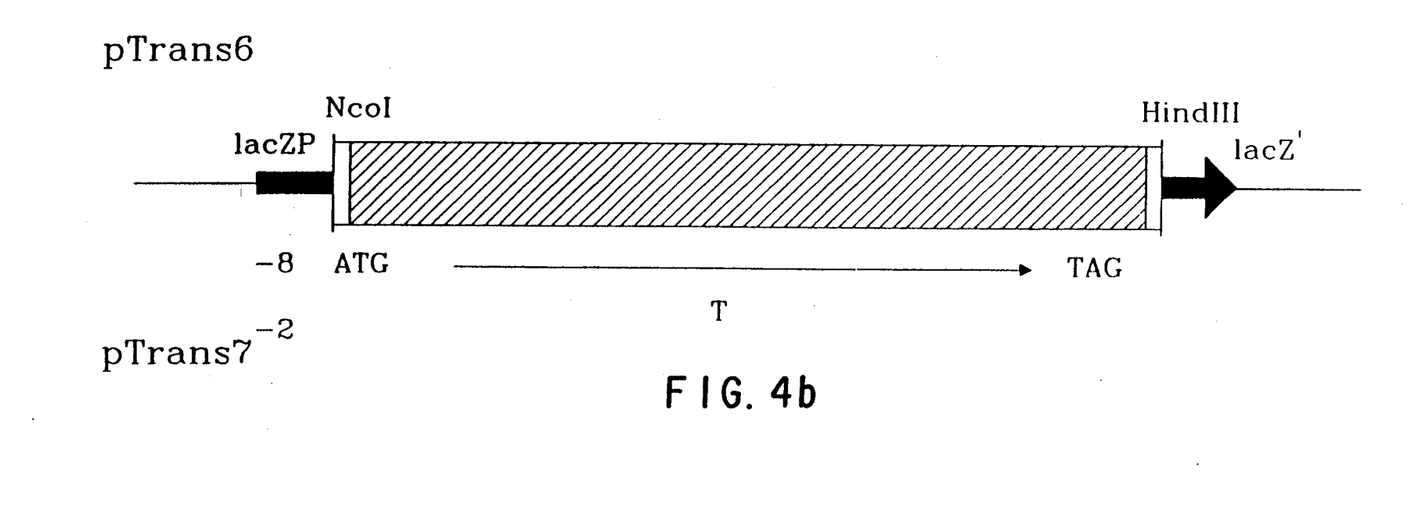

In order to fuse the transaminase structural gene with another promoter, it was necessary to delete as far as possible the non-coding 5' region of the 1.6 kb DraI/BamHI fragment above the ATG start codon. For this purpose, the DNA fragment was truncated from the DraI end using the ExoIII/S1 nuclease technique described above. Two of the deletions prepared in this way [−56 to ATG and −35 to ATG, see Table 5, constructs (I) and (II)] were cloned as SmaI/BamHI fragments behind the lac promoter in the vector pUC12 cut with SmaI/BamHI. The expression plasmids pTrans4 and pTrans5 obtained in this way are depicted in FIG. 4.

In another approach, an NcoI cleavage site was introduced into the transaminase gene in the region of the ATG start codon or in the position −6 by in vitro mutagenesis using the Taq polymerase chain reaction (PCR) technique Higuohi et al. (1988), Nucleic Acids Research 16: 7351-367][see Table 4, constructs (III) and (IV)] the NcoI cleavage site in position −6 does not affect the transaminase structural gene, the mutation in the region of the start codon alters amino acid 2 of the transaminase from Asn to Asp. However, this conservative amino acid replacement has no effect on the activity of the enzyme protein. It was now possible, because of the restriction cleavage sites introduced into the two constructs (III) and (IV), to clone the transaminase structural gene without 5'-non coding sequences, in each case as NcoI/HindIII fragment, behind the lac promoter into the vector pMG12 (pUC12 derivative with modified polylinker: EcoRI-SmaI-BamHI-NcoI-NheI-HgiAI-PstI-KpnI-XbaI-ClaI-SalI-SacII-SphI-PvuI-HindIII), cut with NcoI/HindIII (FIG. 4: plasmids pTrans6 and pTrans7). In order to examine the expression of transaminase with the various gene constructs, E. coli JM103 transformants with the recombinant plasmids pTrans4, pTrans5, pTrans6, pTrans7, as well as pTrans3 (see Example 1) and the vector plasmid pUC12 as control, were cultured in 10 ml of LB medium without and with glucose (0.5%). The L-PPT-specific transaminase activities were measured as described in Example 2 and reported in nmol of L.PPT/min/mg of cells. The results are compiled in Table 5. The enzyme activities with these lac expression plasmids are a factor of approximately 2 higher than with the plasmid pTrans3. All the constructs show catabolite repression in the presence of glucose.

b) tac expression plasmids

Figure 5A:
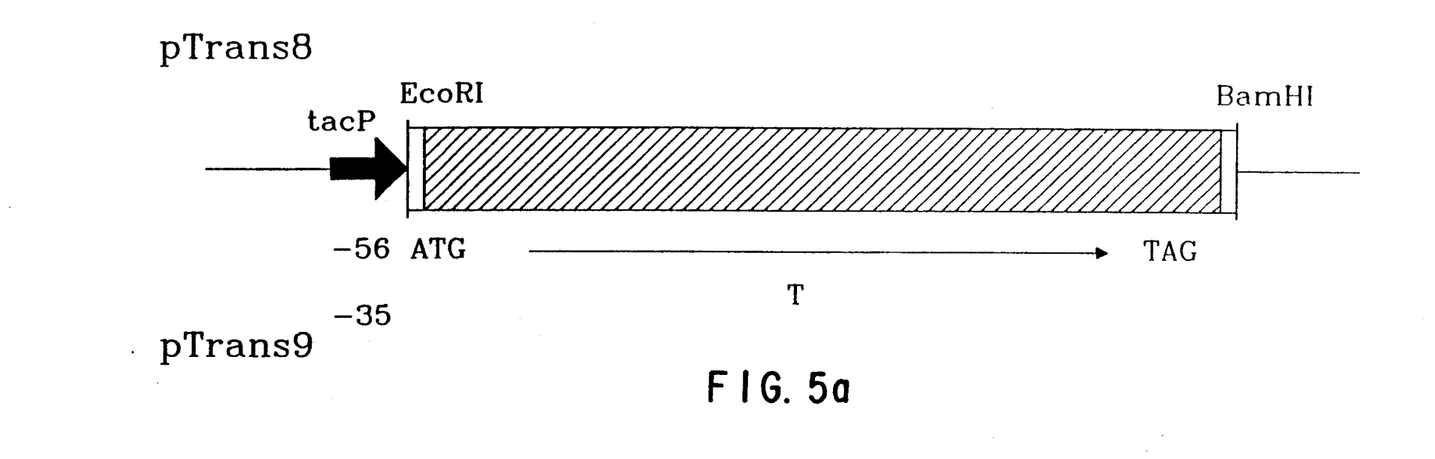
FIG. 5a and b show shows the location of the gene according to the invention in the vectors pTrans8 to pTrans11.
Figure 5B:
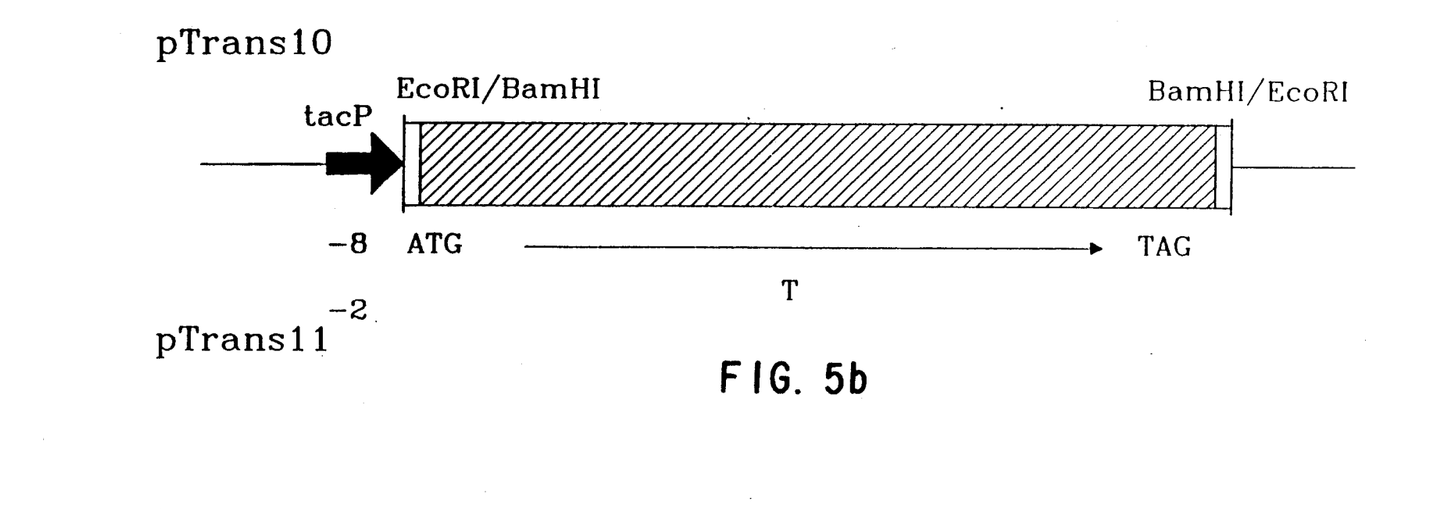
Figure 6A:
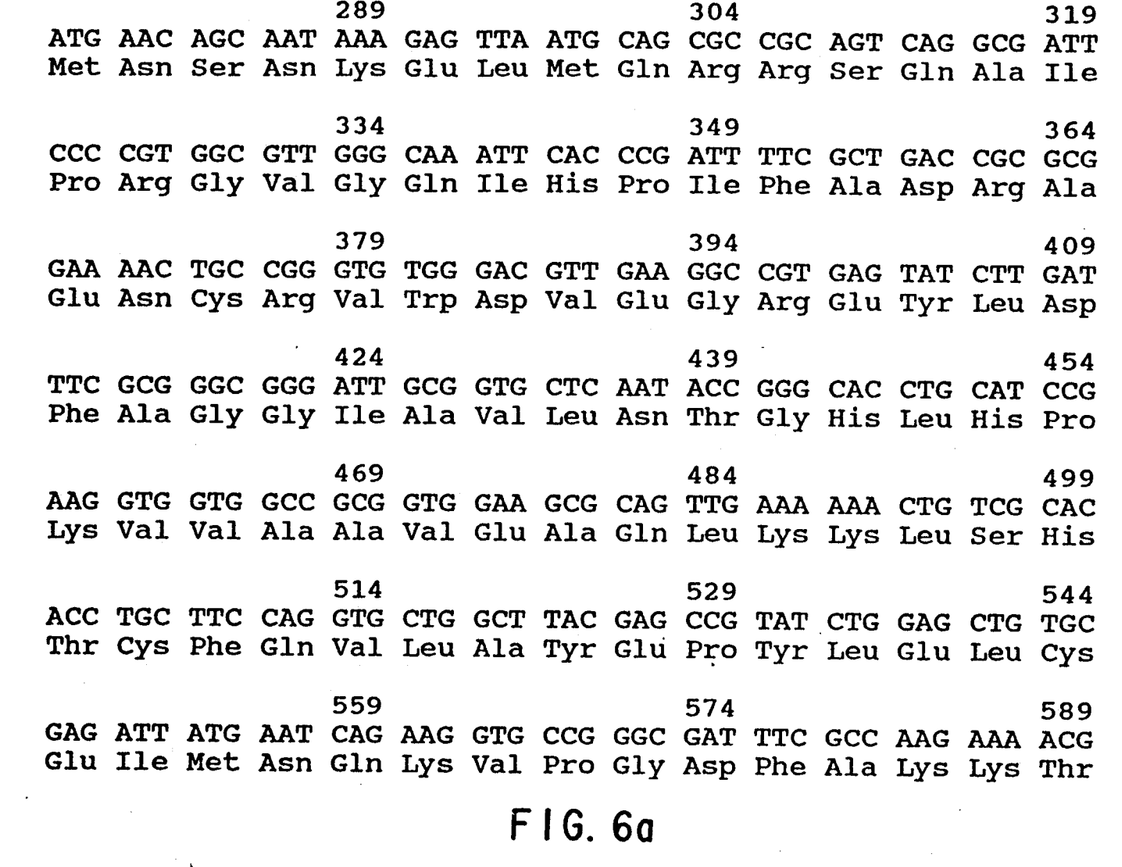
FIG. 6 shows the DNA sequence and amino acid sequence of the gene for a transaminase specific for L-2-amino-4-methylphosphinobutyric acid (L-PPT).
Figure 6B:
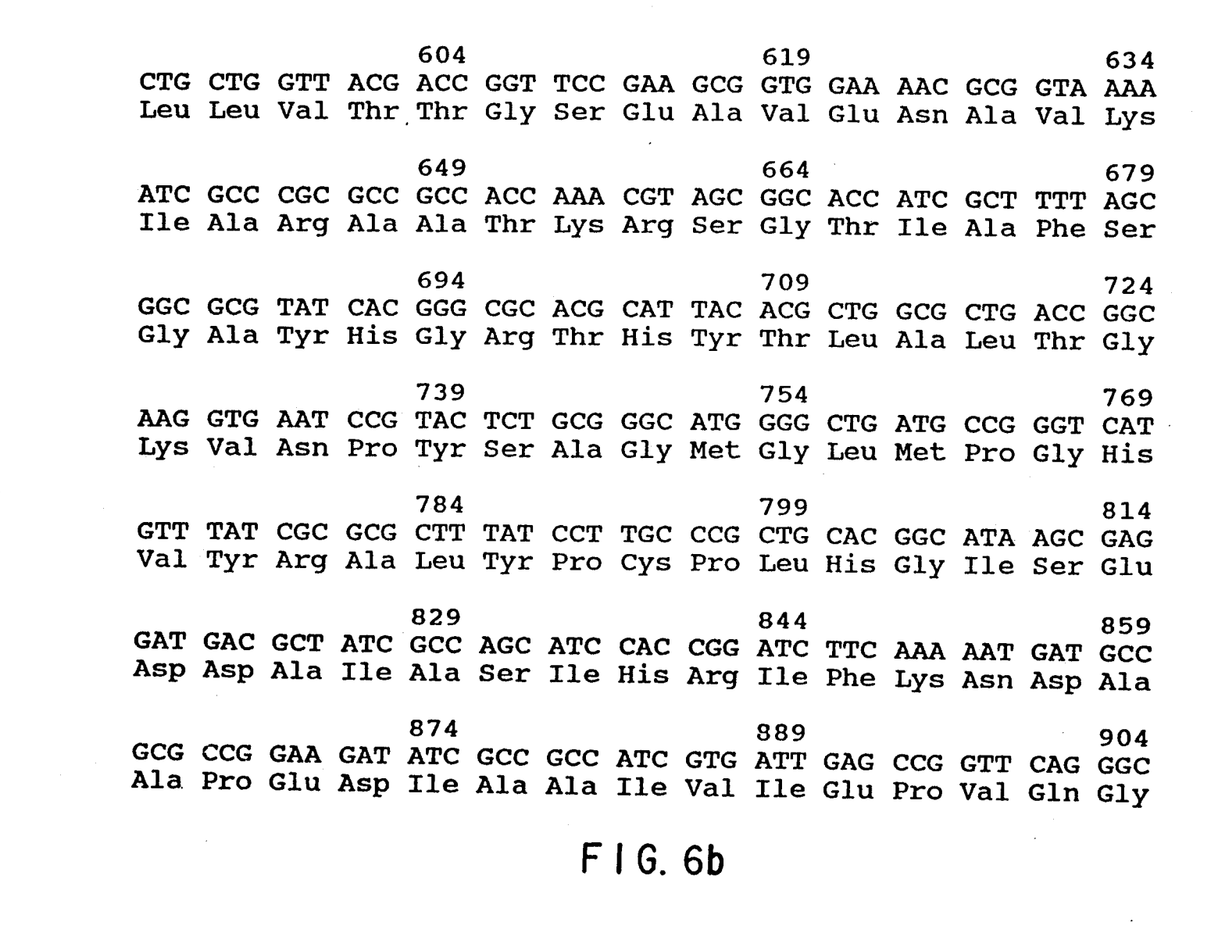
Figure 6C:
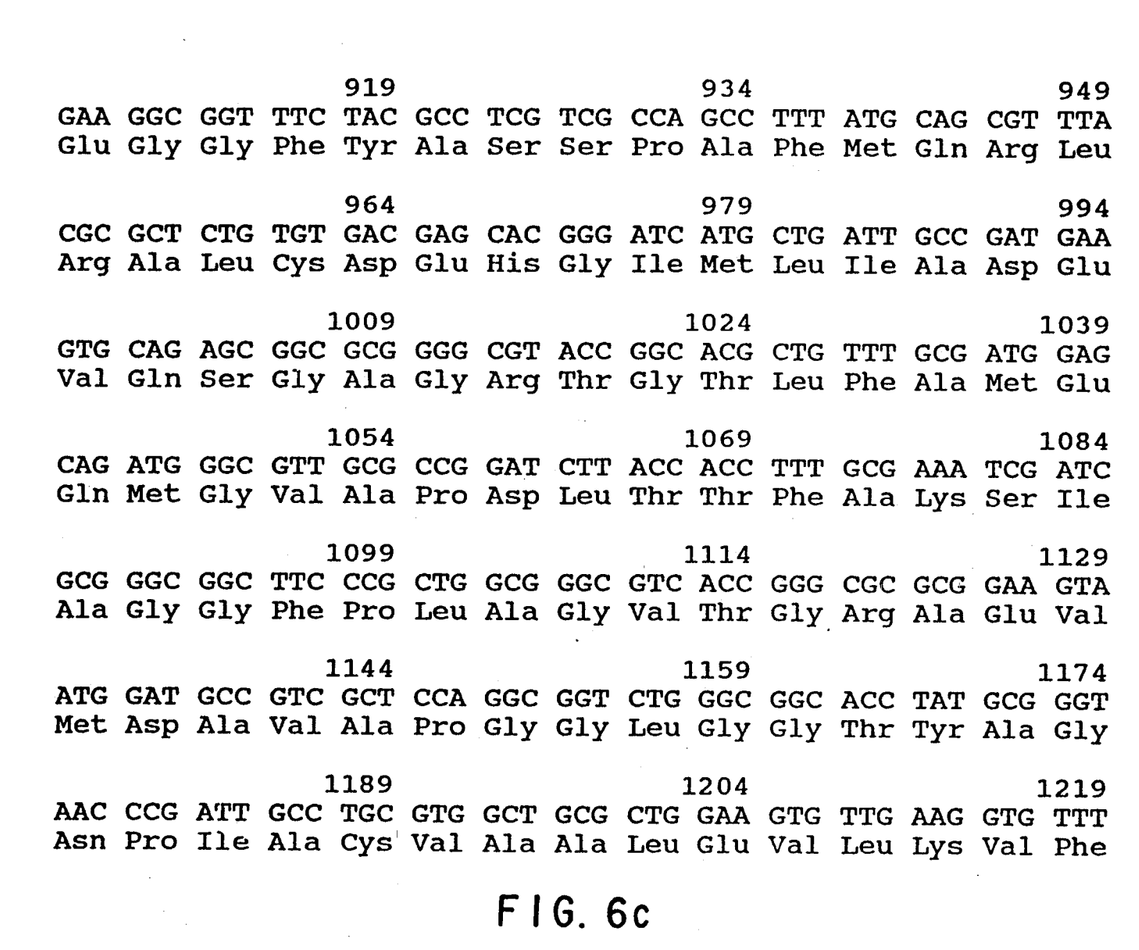
Figure 6D:
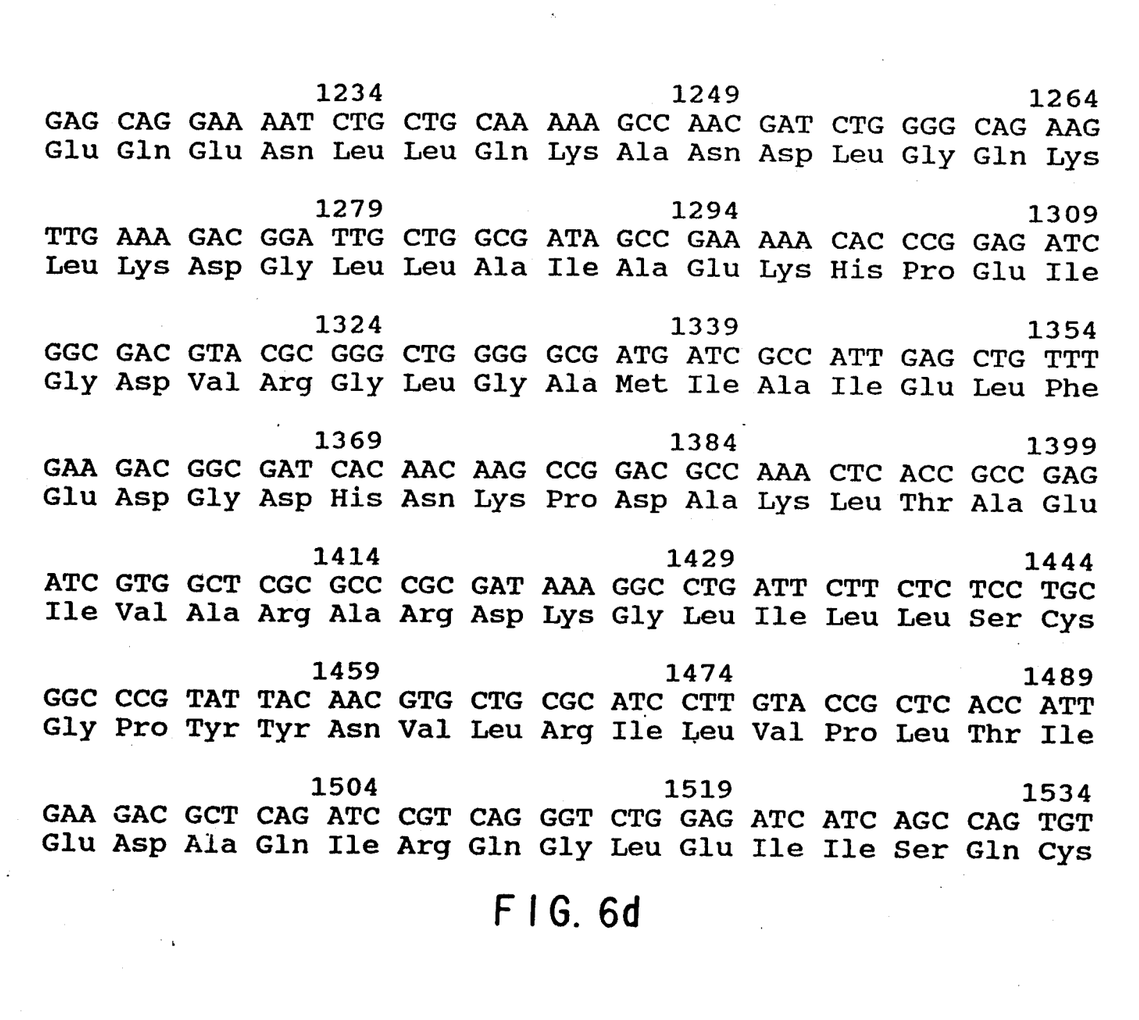
Figure 6E:
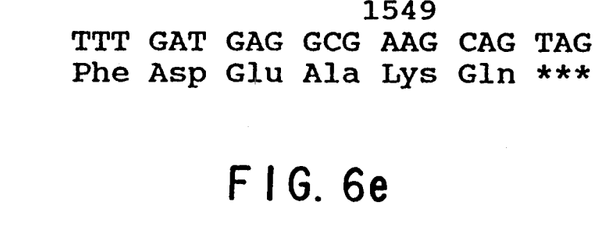

The expression vector pJF118u was used for the expression of the L-PPT transaminase gene with the hybrid tac promoter (lac and trp portions). It is a derivative of pKK223-3 and contains, immediately behind the tac promoter sequence, a polylinker with the restriction cleavage sites EcoRI-SmaI-BamHI-SalI-PstI-HindIII. In addition, the vector expresses the lacI gene coding for the lac repressor, so that the activity of the tac promoter can be induced by IPTG. The tac promoter is not subject to catabolite repression by glucose. The transaminase gene constructs (I) and (II) (ExoIII/S1 nuclease deletions, −56 and −35, respectively, to ATG), which are depicted in Table 4, were cloned as EcoRI/BamHI fragments behind the tac promoter in the vector pJF118u cut with EcoRI/BamHI. FIG. 5 shows the recombinant plasmids pTrans8 and pTrans9 obtained in this way. The transaminase gene constructs (III) and (IV) prepared by in vitro mutagenesis (see Table 4) were isolated as BamHI fragments from the plasmids pTrans6 and pTrans7, and the cohesive ends were filled in with Klenow enzyme. These fragments were cloned behind the tac promoter in pJF118u cut with EcoRI and treated with S1 nuclease. The only isolated subclones which were used further were those which contained the L-PPT transaminase structural gene in the correct orientation to the tac promoter (see FIG. 5, recombinant plasmids pTrans10 and pTrans11). To determine the L-PPT-specific transaminase activities, E. coli JM103 transformants with the recombinant plasmids pTrans8, pTrans9, pTrans10, pTrans11, as well as pTrans3 and the vector plasmid pJF118u as control, were cultured in 10 ml of LB medium without and with glucose (0.5%) and harvested after 8 h. In parallel mixtures, after an O.D.$_{600nm}$ of 0.5 had been reached, the cells were induced with 1 mM IPTG for 4 h and then likewise harvested. The transaminase activities were determined as described in 6.a). The results of the enzyme measurements are compiled in Table 6. All four tac expression plasmids are, by comparison with the plasmid pTrans3, inducible by IPTG and show no catabolite repression in the presence of glucose. The highest enzyme activities in the glucose medium were achieved with the plasmid pTrans11 and are comparable with the values reached with the lac expression constructs in glucose-free medium.

EXAMPLE 7

Production of L-PPT transaminase by fermentation

For the fermentation, the transaminase expression plasmid pTrans7 was transformed into the producer strain E. coli W3110 [Campbell et al. (1978), Proc. Natl. Acad. Sci. USA 75: 2276–2280]. The cells were inoculated into fermentation medium [M9 mineral medium described by Maniatis et al. (1982), Molecular Cloning, A Laboratory Manual, Cold Spring Harbor: 68–69, with 4% maltose as carbon source, 2% casamino acids and 0.4% GABA] and cultivated in a 10 l fermenter (Biostat 5, Braun Melsungen) at a constant stirrer speed (400 rpm), aeration (2 m$^3$/h) and automatic pH control (pH=7.0) and at 35° C. for 24 h. The optical density of the culture, as well as the L-PPT-specific transaminase activity of the cells, were measured during the fermentation by removing control samples. The bacteria were harvested after 24 h at a specific transaminase activity of 0.35 nkat/mg of cells (1 nkat = 1 nmol of L-PPT/sec) and an optical density of 29 (corresponding to a mass of 3 kg wet weight of cells) and subsequently concentrated ten-fold using a cell separator (Westfalia model SA1-02-575). After addition of 20 mM sodium phosphate, pH=7.0, 0.01 mM pyridoxal phosphate, 5 mM 2-mercaptoethanol and 1 mM phenylmethanesulfonyl fluoride (PMSF), the bacteria were disrupted in a microfluidizer (model M-110 TIV, Micro Fluids, Newton USA) under 800 bar. The crude extract was incubated at 70° C. for 10 min, and the cell detritus plus the precipitated proteins were subsequently removed by centrifugation at 6000 xg for 20 min. The supernatant after this treatment contained 16 g of protein with an L-PPT-specific transaminase activity of 7480 nkat/mg of protein. The transaminase activity measured in supernatants, prepared in the same way, of the untransformed producer strain W3110 was only 200 nkat/mg of protein, which corresponds to an approximately 40-fold increase in the enzyme activity by the recombinant plasmid pTrans7. SDS gel analysis of the proteins [Laemmli, U.K. (1970), Nature 227: 680] shows that the L-PPT transaminase is distinctly the predominant protein in the worked-up fermentation supernatants after the thermal precipitation at 70° C. This degree of enrichment of the transaminase is sufficient for the material to be used directly for immobilization of the enzyme on a carrier by the method proposed in German Offenlegungsschrift 3,818,851.

We claim:

TABLE 1

| DraI | | | FspI | | | |
|---|---|---|---|---|---|---|
| TTTAAAGATGAAGCTGATGTGATTGCGCAAGCCAATGACACCGAGTTTGGCCTTGCCGCCTATTTCTACGCC | | | | | | |
| AAATTTCTACTTCGACTACACTAACGCGTTCGGTTACTGTGGCTCAAACCGGAACGGCGGATAAAGATGCGG | | | | | | |
| 12 | 24 | 36 | 48 | 60 | 72 | |

| CGTGATTTAAGCCGCGTCTTCCGCGTGGGCGAAGCGCTGGAGTACGGCATCGTCGGCATCAATACCGGCATT | | | | | | |
| GCACTAAATTCGGCGCAGAAGGCGCACCCGCTTCGCGACCTCATGCCGTAGCAGCCGTAGTTATGGCCGTAA | | | | | | |
| 84 | 96 | 108 | 120 | 132 | 144 | |

TABLE 1-continued

```
ATTTCCAATGAAGTGGCCCCGTTCGGCGGCATCAAAGCCTCGGGTCTGGGTCGTGAAGGTTCGAAGTATGGC
TAAAGGTTACTTCACCGGGGCAAGCCGCCGTAGTTTCGGAGCCCAGACCCAGCACTTCCAAGCTTCATACCG
    156       168       180       192       204       216

ATCGAAGATTACTTAGAAATCAAATATATGTGCATCGGTCTTTAACTGGAGAATGCGAATGAACAGCAATAA
TAGCTTCTAATGAATCTTTAGTTTATATACACGTAGCCAGAAATTGACCTCTTACGCTTACTTGTCGTTATT
    228       240       252       264       276       288

AGAGTTAATGCAGCGCCGCAGTCAGGCGATTCCCCGTGGCGTTGGGCAAATTCACCCGATTTTCGCTGACCG
TCTCAATTACGTCGCGGCGTCAGTCCGCTAAGGGGCACCGCAACCCGTTTAAGTGGGCTAAAAGCGACTGGC
    300       312       324       336       348       360

CGCGGAAAACTGCCGGGTGTGGGACGTTGAAGGCCGTGAGTATCTTGATTTCGCGGGCGGGATTGCGGTGCT
GCGCCTTTTGACGGCCCACACCCTGCAACTTCCGGCACTCATAGAACTAAAGCGCCCGCCCTAACGCCACGA
    372       384       396       408       420       432

SacII
CAATACCGGGCACCTGCATCCGAAGGTGGTGGCCGCGGTGGAAGCGCAGTTGAAAAAACTGTCGCACACCTG
GTTATGGCCCGTGGACGTAGGCTTCCACCACCGGCGCCACCTTCGCGTCAACTTTTTTGACAGCGTGTGGAC
    444       456       468       480       492       504

CTTCCAGGTGCTGGCTTACGAGCCGTATCTGGAGCTGTGCGAGATTATGAATCAGAAGGTGCCGGGCGATTT
GAAGGTCCACGACCGAATGCTCGGCATAGACCTCGACACGCTCTAATACTTAGTCTTCCACGGCCCGCTAAA
    516       528       540       552       564       576

CGCCAAGAAAACGCTGCTGGTTACGACCGGTTCCGAAGCGGTGGAAAACGCGGTAAAAATCGCCCGCGCCGC
GCGGTTCTTTTGCGACGACCAATGCTGGCCAAGGCTTCGCCACCTTTTGCGCCATTTTTAGCGGGCGCGGCG
    588       600       612       624       636       648

CACCAAACGTAGCGGCACCATCGCTTTTAGCGGCGCGTATCACGGGCGCACGCATTACACGCTGGCGCTGAC
GTGGTTTGCATCGCCGTGGTAGCGAAAATCGCCGCGCATAGTGCCCGCGTGCGTAATGTGCGACCGCGACTG
    660       672       684       696       708       720

BssHII
CGGCAAGGTGAATCCGTACTCTGCGGGCATGGGGCTGATGCCGGGTCATGTTTATCGCGCGCTTTATCCTTG
GCCGTTCCACTTAGGCATGAGACGCCCGTACCCCGACTACGGCCCAGTACAAATAGCGCGCGAAATAGGAAC
    732       744       756       768       780       792

CCCGCTGCACGGCATAAGCGAGGATGACGCTATCGCCAGCATCCACCGGATCTTCAAAAATGATGCCGCGCC
GGGCGACGTGCCGTATTCGCTCCTACTGCGATAGCGGTCGTAGGTGGCCTAGAAGTTTTTACTACGGCGCGG
    804       816       828       840       852       864

EcoRV
GGAAGATATCGCCGCCATCGTGATTGAGCCGGTTCAGGGCGAAGGCGGTTTCTACGCCTCGTCGCCAGCCTT
CCTTCTATAGCGGCGGTAGCACTAACTCGGCCAAGTCCCGCTTCCGCCAAAGATGCGGAGCAGCGGTCGGAA
    876       888       900       912       924       936

TATGCAGCGTTTACGCGCTCTGTGTGACGAGCACGGGATCATGCTGATTGCCGATGAAGTGCAGAGCGGCGC
ATACGTCGCAAATGCGCGAGACACACTGCTCGTGCCCTAGTACGACTAACGGCTACTTCACGTCTCGCCGCG
    948       960       972       984       996      1008

PvuI
                                                                    ClaI
GGGGCGTACCGGCACGCTGTTTGCGATGGAGCAGATGGGCGTTGCGCCGGATCTTACCACCTTTGCGAAATC
CCCCGCATGGCCGTGCGACAAACGCTACCTCGTCTACCCGCAACGCGGCCTAGAATGGTGGAAACGCTTTAG
    1020      1032      1044      1056      1068      1080

PvuI
ClaI                                          BssHII
 GATCGCGGGCGGCTTCCCGCTGGCGGGCGTCACCGGGCGCGCGGAAGTAATGGATGCCGTCGCTCCAGGCGG
 CTAGCGCCCGCCGAAGGGCGACCGCCCGCAGTGGCCCGCGCGCCTTCATTACCTACGGCAGCGAGGTCCGCC
    1092      1104      1116      1128      1140      1152

TCTGGGCGGCACCTATGCGGGTAACCCGATTGCCTGCGTGGCTGCGCTGGAAGTGTTGAAGGTGTTTGAGCA
AGACCCGCCGTGGATACGCCCATTGGGCTAACGGACGCACCGACGCGACCTTCACAACTTCCACAAACTCGT
    1164      1176      1188      1200      1212      1224

GGAAAATCTGCTGCAAAAAGCCAACGATCTGGGGCAGAAGTTGAAAGACGGATTGCTGGCGATAGCCGAAAA
CCTTTTAGACGACGTTTTTCGGTTGCTAGACCCCGTCTTCAACTTTCTGCCTAACGACCGCTATCGGCTTTT
    1236      1248      1260      1272      1284      1296

ACACCCGGAGATCGGCGACGTACGCGGGCTGGGGGCGATGATCGCCATTGAGCTGTTTGAAGACGGCGATCA
TGTGGGCCTCTAGCCGCTGCATGCGCCCGACCCCCGCTACTAGCGGTAACTCGACAAACTTCTGCCGCTAGT
    1308      1320      1332      1344      1356      1368

StuI
CAACAAGCCGGACGCCAAACTCACCGCCGAGATCGTGGCTCGCGCCCGCGATAAAGGCCTGATTCTTCTCTC
GTTGTTCGGCCTGCGGTTTGAGTGGCGGCTCTAGCACCGAGCGCGGGCGCTATTTCCGGACTAAGAAGAGAG
    1380      1392      1404      1416      1428      1440
```

TABLE 1-continued

```
                              FspI
CTGCGGCCCGTATTACAACGTGCTGCGCATCCTTGTACCGCTCACCATTGAAGACGCTCAGATCCGTCAGGG
GACGCCGGGCATAATGTTGCACGACGCGTAGGAACATGGCGAGTGGTAACTTCTGCGAGTCTAGGCAGTCCC
         1452        1464        1476        1488        1500        1512

TCTGGAGATCATCAGCCAGTGTTTTGATGAGGCGAAGCAGTAGCGCCGCTCCTATGCCGGAGAGCACTGCGC
AGACCTCTAGTAGTCGGTCACAAAACTACTCCGCTTCGTCATCGCGGCGAGGATACGGCCTCTCGTGACGCG
         1524        1536        1548        1560        1572        1584

BamHI
GTCTTGTCCGGCCTACGGGGATCC
CAGAACAGGCCGGATGCCCCTAGG
         1596        1608
```

TABLE 4

(I)  5'                                                                                    3'
     CGAAGATTACTTAGAAATCAAATATATGTGCATCGGTCTTTAACTGGAGAATGCGA ATG AAC AGC AAT ...
                                                             Met Asn Ser Asn ...

(II)                                          5'                                          3'
                                              ATATATGTGCATCGGTCTTTAACTGGAGAATGCGA ATG AAC AGC AAT ...
                                                                                 Met Asn Ser Asn ...

(III)                                                            5' NcoI                  3'
                                                                 CCATGGGA ATG AAC AGC AAT ...
                                                                          Met Asn Ser Asn ...

(IV)                                                                     5' NcoI         3'
                                                                         CC ATG GAC AGC AAT ...
                                                                            Met Asp Ser Asn ...

TABLE 5

L-PPT-specific transaminase activities in
transformants of E. coli JM103 with various lac
expression plasmids.

| Plasmid: | Medium: | Spec. transaminase activity [nmol of L-PPT/min/mg of cells]: |
|---|---|---|
| pTrans4 | LB | 22.8 |
| | LB + 0.5% gluc. | 0.6 |
| pTrans5 | LB | 25.7 |
| | LB + 0.5% gluc. | 1.2 |
| pTrans6 | LB | 24.5 |
| | LB + 0.5% gluc. | 1.2 |
| pTrans7 | LB | 24.9 |
| | LB + 0.5% gluc. | 0.9 |
| pTrans3 | LB | 9.7 |
| | LB + 0.5% gluc. | 0.9 |
| pUC12 | LB | 0.9 |
| | LB + 0.5% gluc. | 0.1 |

TABLE 6

L-PPT-specific transaminase activities in
transformants of E. coli JM103 with various tac
expression plasmids.

| Plasmid: | Medium: | Spec. transaminase activity [nmol of L-PPT/min/mg of cells]: |
|---|---|---|
| pTrans8 | LB | 11.4 |
| | LB + 1 mM IPTG | 20.5 |
| | LB + 0.5% gluc. | 2.6 |
| | LB + 0.5% gluc. + 1 mM IPTG | 12.9 |
| pTrans9 | LB | 9.6 |
| | LB + 1 mM IPTG | 21.7 |
| | LB + 0.5% gluc. | 3.9 |
| | LB + 0.5% gluc. + 1 mM IPTG | 11.3 |
| pTrans10 | LB | 2.3 |
| | LB + 1 mM IPTG | 16.6 |
| | LB + 0.5% gluc. | 0.7 |
| | LB + 0.5% gluc. + 1 mM IPTG | 4.5 |
| pTrans11 | LB | 5.9 |
| | LB + 1 mM IPTG | 20.9 |
| | LB + 0.5% gluc. | 2.2 |
| | LB + 0.5% gluc. + 1 mM IPTG | 22.1 |
| pTrans3 | LB | 10.2 |
| | LB + 1 mM IPTG | 10.7 |
| | LB + 0.5% gluc. | 0.3 |
| | LB + 0.5% gluc. + 1 mM IPTG | 0.4 |
| pJF 118u | LB | 1.0 |
| | LB + 1 mM IPTG | 0.9 |
| | LB + 0.5% gluc. | 0.2 |
| | LB + 0.5% gluc. + 1 mM IPTG | 0.3 |

1. An isolated and purified 1.6 kb DraI/BamHI fragment from the genome of E. coli DH 1, which fragment contains the structural gene coding for a transaminase specific for L-3-amino-4methylphosphinobutyric acid (L-PPT), said gene having the DNA sequence shown in FIG. 6.

2. An isolated, purified, structural gene coding for an enzyme having the amino acid sequence shown in FIG. 6.

3. A plasmid containing a gene as claimed in claim 1.

4. A plasmid containing a gene as claimed in claim 2.

5. A microorganism containing a plasmid as claimed in claim 3.

6. A microorganism containing a plasmid as claimed in claim 4.

7. E. coli containing a plasmid as claimed in claim 3.

8. E. coli containing a plasmid as claimed in claim 4.

* * * * *

UNITED STATES PATENT AND TRADEMARK OFFICE
CERTIFICATE OF CORRECTION

PATENT NO. : 5,221,737
DATED : June 22, 1993
INVENTOR(S) : Klaus Bartsch et al.

It is certified that error appears in the above-indentified patent and that said Letters Patent is hereby corrected as shown below:

Claim 1, column 12, line 55, change
"L-3-amino-4methylphosphinobutyric"
to --L-2-amino-4-methylphosphinobutyric--.

Signed and Sealed this

Twelfth Day of April, 1994

*Attest:*

BRUCE LEHMAN

*Attesting Officer*

*Commissioner of Patents and Trademarks*